(12) United States Patent
Hujer

(10) Patent No.: US 11,937,969 B2
(45) Date of Patent: Mar. 26, 2024

(54) SYSTEM AND METHOD FOR RECORDING POSITIONAL INFORMATION OF MOVING IMAGE MODALITY COMPONENTS AT THE EXACT ACQUISITION MOMENTS OF A TOMOGRAPHIC IMAGE CAPTURE SEQUENCE

(71) Applicant: AGFA NV, Mortsel (BE)

(72) Inventor: Oskar Hujer, Munich (DE)

(73) Assignee: Agfa NV, Mortsel (BE)

( * ) Notice: Subject to any disclaimer, the term of this patent is extended or adjusted under 35 U.S.C. 154(b) by 321 days.

(21) Appl. No.: 17/610,189

(22) PCT Filed: May 11, 2020

(86) PCT No.: PCT/EP2020/063063
§ 371 (c)(1),
(2) Date: Nov. 10, 2021

(87) PCT Pub. No.: WO2020/229417
PCT Pub. Date: Nov. 19, 2020

(65) Prior Publication Data
US 2022/0257211 A1    Aug. 18, 2022

(30) Foreign Application Priority Data

May 14, 2019 (EP) .................................... 19174256

(51) Int. Cl.
*A61B 6/00* (2006.01)
*A61B 6/02* (2006.01)
(Continued)

(52) U.S. Cl.
CPC .............. *A61B 6/547* (2013.01); *A61B 6/025* (2013.01); *A61B 6/027* (2013.01); *A61B 6/4452* (2013.01); *A61B 6/467* (2013.01); *G06T 11/005* (2013.01)

(58) Field of Classification Search
CPC ......... A61B 6/547; A61B 6/025; A61B 6/027; A61B 6/4452; A61B 6/467; A61B 6/582;
(Continued)

(56) References Cited

U.S. PATENT DOCUMENTS

2015/0265223 A1    9/2015   Simon et al.
2015/0332485 A1*  11/2015   Klausz ................... A61B 6/025
                                                                        378/8

FOREIGN PATENT DOCUMENTS

EP            2820450 B1    4/2019
WO    WO 2013/128363 A2    9/2013

OTHER PUBLICATIONS

European Patent Office, International Search Report in International Patent Application No. PCT/EP2020/063063, dated Sep. 9, 2020, 4 pp.

(Continued)

*Primary Examiner* — David P Porta
*Assistant Examiner* — Mamadou Faye
(74) *Attorney, Agent, or Firm* — Leydig, Voit & Mayer, Ltd.

(57) ABSTRACT

The present invention relates generally to a method and a system that allows to accurately calculate positional information of moving image modality components for a sequence of tomographic exposures. The method allows to accurately determine the exact positions of said movable image modality components, and thus the acquisition geometry at the time of the tomographic acquisition, which allows a more accurate image reconstruction.

7 Claims, 1 Drawing Sheet

(51) Int. Cl.
*A61B 6/46* (2024.01)
*G06T 11/00* (2006.01)
(58) Field of Classification Search
CPC ....... A61B 6/035; A61B 6/542; G06T 11/005; G06T 2211/412
See application file for complete search history.

(56) References Cited

OTHER PUBLICATIONS

European Patent Office, Written Opinion in International Patent Application No. PCT/EP2020/063063, dated Sep. 9, 2020, 6 pp.

\* cited by examiner

SYSTEM AND METHOD FOR RECORDING POSITIONAL INFORMATION OF MOVING IMAGE MODALITY COMPONENTS AT THE EXACT ACQUISITION MOMENTS OF A TOMOGRAPHIC IMAGE CAPTURE SEQUENCE

CROSS-REFERENCE TO RELATED APPLICATIONS

This patent application is the U.S. national phase of copending International Patent Application No. PCT/EP2020/063063, filed May 11, 2020, which claims the benefit of European Patent Application No. 19174256.8, filed May 14, 2019.

TECHNICAL FIELD

The present invention relates to the tomographic imaging systems used in medicine. Different tomographic techniques are in use in modern medicine of which CT (computed tomography) and digital tomosythesis are the best known examples. In all cases, the production of tomographic images is based on a mathematical procedure for tomographic reconstruction, such as X-ray computed tomography technically is being produced from multiple projectional radiographs. Tomosynthesis, also called digital tomosynthesis (DTS), is a method for performing high-resolution limited-angle tomography at radiation dose levels comparable with projectional radiography. The technique has been studied for a variety of clinical applications, including vascular imaging, dental imaging, orthopedic imaging, mammographic imaging, musculoskeletal imaging, and chest imaging.

In tomosynthesis, only a limited rotation angle of the source and detector around the subject is required (e.g., 15-60 degrees) resulting in a lower number of discrete exposures (e.g., 7-51), if compared with CT (where at least 180 degrees of rotation are required). This incomplete set of projections is digitally processed to yield images similar to conventional tomography with a limited depth of field. Because the image processing is digital, a series of slices at different depths and with different thicknesses can be reconstructed from the same acquisition. However, since fewer projections are needed than CT to perform the reconstruction, radiation exposure and cost are both reduced.

Tomosynthesis thus requires that the conventional X-ray modality on which the technique is performed supports a limited angle rotation around the patient by the X-ray source and digital image detector. Additionally, in order to allow a calculated image reconstruction, the exact positions of the X-ray source and digital image detector have to be known when the different image acquisitions take place.

BACKGROUND OF THE INVENTION

In the art, different approaches have been proposed to try to obtain and record the exact positions of the X-ray source and digital image detector which are crucial in the image reconstruction calculation. A preferred method is to obtain this information indirectly by measuring the positions of the (moving) components that contribute to the movements of the X-ray source and digital image detector in the tomographic sequence of a tomosynthesis imaging system. This positional data may be considered as a collection of positional information expressed as a set of coordinates or angles, and an identifier identifying the moving image modality component. The positional data is encoded in digital format and is transmitted as digital data over a digital communication interface (such as a computer data network or alike).

A tomosynthesis imaging system typically comprises a number of movable image modality components. The terminology of a movable image modality component that is used in the context of this invention, is defined as a mechanical building block that contributes to the tomographic trajectory performed by the X-ray source and digital imaging detector. There are two types of movable image modality components contributing to the tomographic trajectory in a generic tomosynthesis radiographic system; the devices driving and controlling the movement of the X-ray source and the devices driving the movement of the detector. The movable image components are thus in practice and for example an overhead tube crane (carrying an X-ray collimator fitting an X-ray tube), or any other type of X-ray source suspension (such as for instance: a free-standing mount), and for instance a detector bucky fitted into a wallstand or a table. The physical coordinates of the "active" component (detector or X-ray source) need to be determined very accurately in order to be able to reconstruct the acquisition geometry of the tomographic system at the time of an image acquisition.

A positional event is an event that marks the presence of a certain movable image modality component in a certain physical position on the acquisition trajectory. An acquisition event is an event that marks the start or completion of an image acquisition performed by the digital image detector. In order to associate the positional information of the movable image modality components to an acquisition event, the association of the exact position and the acquisition event will be made via the time parameter of the acquisition event. In practice, can the acquisition event for instance trigger an instant query for the positional data of the movable image modality components, in order to collect the positional data in real-time.

In other systems known in the art, a central master clock is used to time-stamp events that are associated either with a positional event or an acquisition event, or both. In such a case, event data are generated by the movable image modality components or the detector on demand of a component putting out a query for the positional information. For instance, may an acquisition event reported by the detector trigger the master clock to log the time, and at the same time trigger a query to the movable image modality components to report their positional information. The data may be collected by a central component that is associated with said master clock. The result is that all incoming information (positional information or image information) that is associated with the above mentioned events will be tagged with timing data provided by the master clock. In such case, a time-stamp will be attributed to an incoming event in real-time (i.e. as soon as an event is announced or is received by the central component that is associated with the master clock).

In the case of a positional event, the component of which the position is recorded reports its position actively to the central component that runs the master clock, and the time-stamp of the reporting action (time of arrival of the positional report) is used as the time-stamp of the positional event itself. The problem with this approach is that the delay in the reporting or latency of the reporting action causes inaccuracies. This is the reason for which these types of implementations are optimized for very fast (or real-time)

data reporting capabilities between the moving image modality component and the module running the central master clock.

As such, the central component receives positional event data upon its demand from different components as fast as possible in response to the trigger. These data are then stored at the central component. This mechanism implies that the accuracy of the time-stamp may suffer in case of latency on the data network.

Another embodiment often applied in such systems is that the central component at predetermined central clock-driven intervals polls the moving components for their positional information. Likewise here, a signal lag on the data network between the central and the moving components may result in an inaccurate association of the time-stamp and the respective positional information. It is for this reason that many of such systems are relying on a real-time system architecture in order to minimize the latencies. However, even these special measures often do not guarantee the required accuracy, as they are still prone to latency due to signal bottle-necks or signal collisions.

It is the purpose of this invention to overcome the above mentioned problems; the here described solution intends to overcome the reported shortcomings in state of the art systems.

SUMMARY OF INVENTION

The present invention provides a method and a system that accurately records positional information of moving image modality components during a sequence of tomographic exposures, in order to allow an image reconstruction algorithm to accurately reconstruct the images. A tomography image reconstruction algorithm requires that the orientation and position of the X-ray source and digital image detector is known very accurately at the moments when the tomographic images are acquired in order to perform adequately. The system of the invention relies on the use of a series of (preferably identical) accurate clocks that are associated with each of the participating components in an acquisition, and a single hardware trigger that is used to signal the accurate clocks to synchronize their times.

More specifically, the invention provides a system for calculating positional information of multiple movable image modality components for an acquisition event that occurs during a tomographic image capture sequence, comprising a positioner module, that comprises an input interface configured to receive time-stamped positional information from said multiple moveable image modality components at multiple time intervals during said tomographic image capture sequence, and said input interface configured to receive a time-stamp value query of said acquisition event, a memory to store said time-stamped positional information for said multiple moveable image modality components at said multiple time intervals, a processing unit that calculates (accurate) positional information by interpolation of said stored time-stamped positional information of said movable image modality components for a time-stamp value query of said acquisition event, wherein the interpolated results are calculated relative to a synchronization signal, an output interface to provide (accurate) positional information on all of said moveable image modality components in response to said time-stamp value query calculated by said processing unit, and a clock associated with each of said multiple movable modality components to provide a time-stamp for each positional event of said movable modality component at multiple time intervals during said tomographic image capture sequence, wherein each of said clocks is interconnected in order to accept said synchronization signal to synchronize the times of said clocks.

In the context of the invention, positional information has to be interpreted as the information or data that completely and unambiguously describes the position and/or orientation of an object in space. Since there are different ways to unambiguously describe a position in space, such as the cartesian coordinate system or polar coordinate system, the actual data (or numbers) that express such a position in Euclidian space may vary. In the case that not only the position, but also a direction (of for instance the X-ray source angle, or the image detector plane) has to be determined, the positional information may be expressed as a vector. Positional information is thus expressed as positional data in the form of a set of coordinates and/or angles. A positional event is the moment in time at which such positional data is collected. Positional event data comprises both the positional data and the event time of the positional event.

In the invention, reference is made to movable modality components which are tracked and for which accurate positions are determined or measured. These movable modality components, are thus discrete components which are physical parts of an image modality. Depending on the type of tomographic modality, these movable parts may be different and may for instance cause translations or rotations of the X-ray source and/or the digital imaging detector.

A tomosynthesis modality consists at least of a movable X-ray source, which can be moved according to a controlled trajectory, and this—optionally—in combination with a coordinated movement of a digital image detector. In tomosynthesis, different (conventional) radiographies are acquired of a patient or object under different inclinations of the X-ray source/image detector combination. So, in the context of this invention, there are typically two movable modality components to be considered for a tomosynthesis modality.

The first movable modality component for which the position is tracked is the X-ray source or, alternatively, a device mounting the X-ray source or a part that is physically connected to the X-ray source, such as the collimator or a moving part of the ceiling suspension determining the tomographic trajectory. Depending on which of these components is able to report positional information digitally will determine which exact movable component will be tracked. Since, in the end, it is the purpose of the invention to be able to determine the exact position and orientation of the X-ray source (in order to be able to fully determine the acquisition geometry determined by the source in combination with the detector), the positional information will be associated with an arbitrary chosen point on any of these components that determine the position and orientation of the X-ray source.

The second movable modality component is the digital image detector, or the bucky that fits the detector. In a typical tomographic trajectory of a tomosynthesis modality system, the bucky (carrying the detector) will travel in the opposite direction of the X-ray source trajectory so that the acquisition axis rotates around a central point that lies within the body of the patient or object.

An acquisition event is defined here as a time-based action or occurrence at which an image acquisition takes place. A tomographic acquisition consists of series of discrete radiography acquisitions taken under a different angle. So, it can be stated that during a tomosynthesis acquisition, multiple acquisition events take place, each associated with a particular moment in time. The multiple acquisition events determine or define the tomographic acquisition sequence, which is in fact a number of image acquisitions at predetermined times (and consequently predetermined positions). The tomosynthesis reconstruction will be based on the combination of the image data and the knowledge of the acquisition geometry of these respective image data.

In the context of this invention, a positioner module has to be interpreted as a functional electronic module which may be implemented as a computer system running a computer program, that has at least an input and output interface, and that is configured to perform the steps as set out in the description of the invention below. The positioner comprises a number of essential components or modules, such as the mentioned input and output interfaces, a memory and a processing unit. The positioner module may thus be implemented as a computer module typically already comprising the above mentioned components natively.

In the context of the invention, the digital clocks are accurate electronic digital components providing independent and accurate clock signals to either any of the movable digital image components in order for them to associate said clock signal to any of their triggered positional events, or to a different module (such as for instance the positioner module) that performs this association between the associated digital clock and the movable digital image component's positional event data. A separate digital clock has to be associated with the digital X-ray detector in order to be able to associate an accurate and synchronised time-stamp to any image acquisition event performed on this digital X-ray detector.

The involved digital clocks are connected to each other via a single (and simple) synchronisation wire and are also connected to the system or module that gives the synchronisation signal. The single synchronisation wire is preferably an electrical connection (i.e. a conducting hardware wire) in order to limit any possible latency effects in the synchronisation step of the digital clocks.

Further advantages and embodiments of the present invention will become apparent from the following description and drawings.

DESCRIPTION OF EMBODIMENTS

In the following detailed description, reference is made in sufficient detail to the above referenced drawings, allowing those skilled in the art to practice the embodiments explained below.

Figure 1:
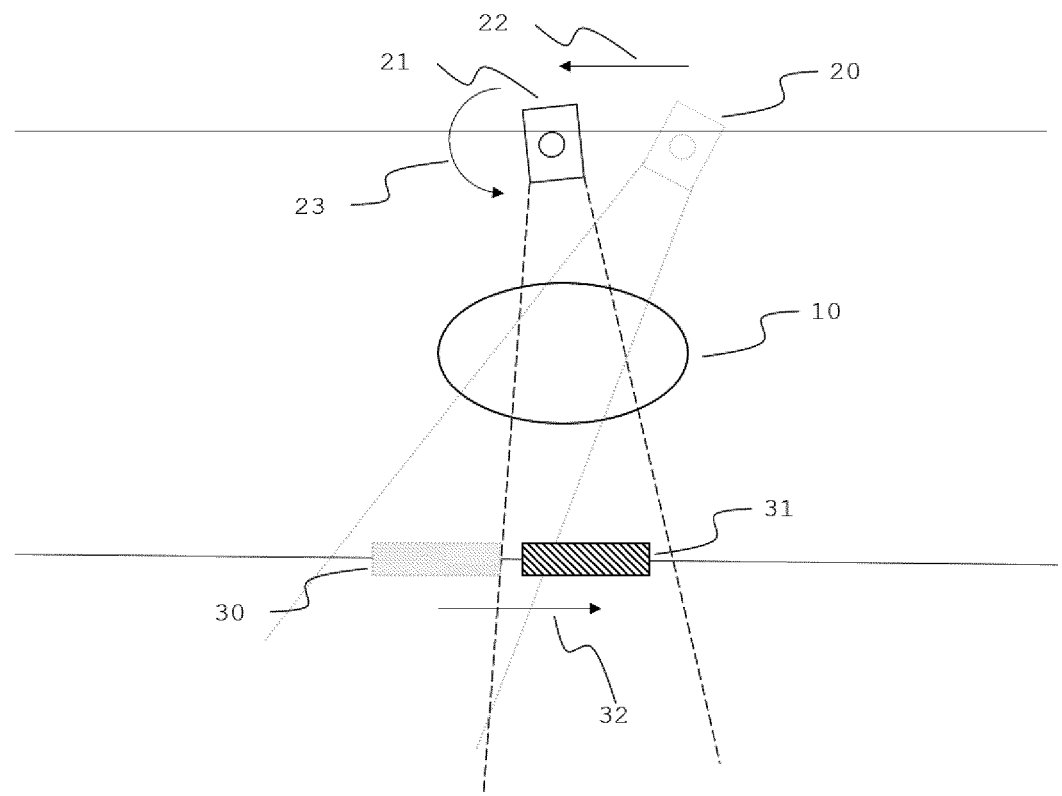
FIG. 1 gives a schematic representation of a tomosynthesis X-ray system wherein an object or a patient [10] is subjected to a tomographic acquisition sequence consisting of two radiographic acquisitions performed by an X-ray source in a first position [20] and a second position [21], to which a digital imaging detector is aligned in two corresponding positions [30] and [31] respectively. The first acquisition is thus performed when the X-ray source is in position [20] and the digital imaging detector is in position [30], after which the X-ray source is moved [22] and rotated [23] into a second position [21] while the digital imaging detector is moved to a position [32], while exposing the object or patient from a different incidence angle. The detector thus travels in an opposite direction as the X-ray source when performing the tomographic trajectory. It is noted that the movements [22], [23] and [32] are physically performed by three movable image modality components, whose positional data (2 sets of coordinates and one angle) are sent to the positioner module.
Figure 2:
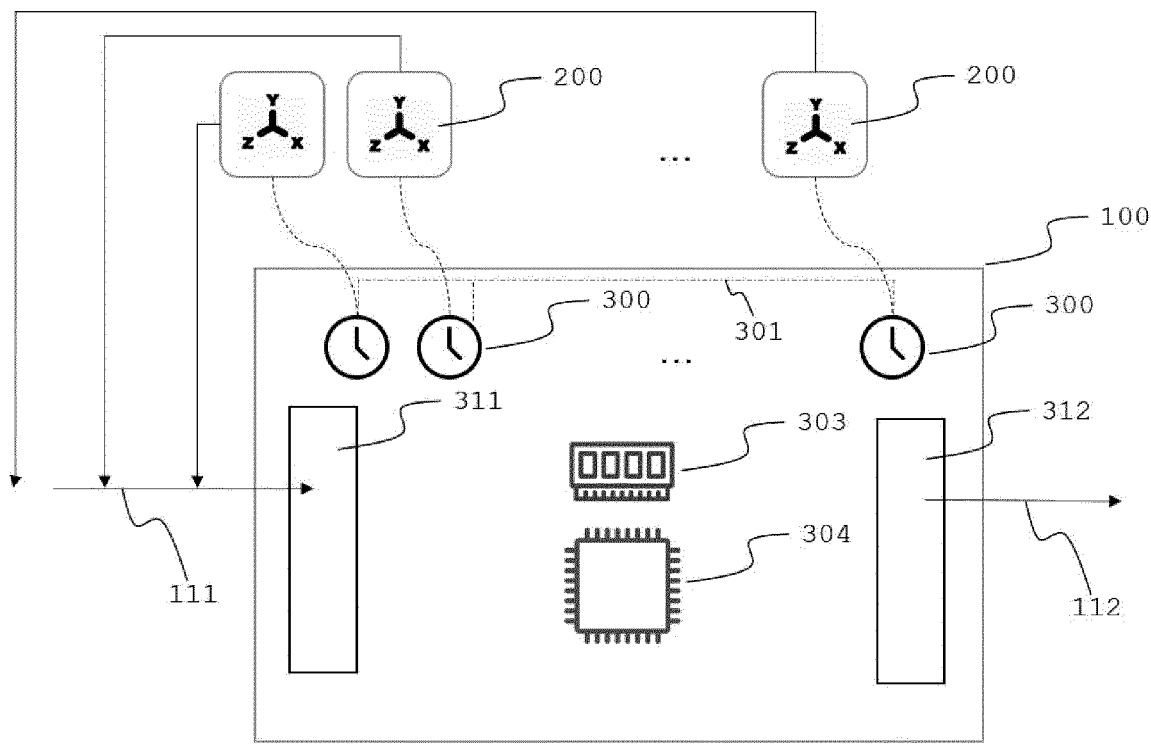
FIG. 2 is a schematic representation of an embodiment of a positioner module [100] in which a series of digital clocks [300] is integrated. The digital clocks are electrically connected with each other via an electrical wire [301] to accept simultaneously a synchronization signal. The positioner module [100] further comprises an input interface [311] accepting input signals [111] and an output interface [312] providing output signals [112]. Further, the positioner module comprises a memory [303] to store time-stamped positional data from positional events from the movable image modality components [200] which are part of the tomosynthesis system. The time-stamped positional data are sent by the movable image modality components [200] as an input signal [111] via the input interface [311] to the memory [303] (as indicated by the arrows between in the drawing). It is noted that the digital clocks [300] each are associated with one movable image modality component [200].

In a first embodiment of the invention, a combination of a set of digital clocks [300] and a positioner module [100] is proposed to manage all the functions required for the working of the invention. The combination of digital clocks and the positioner component may be integrated into a single physical unit such that it may be implemented or applied as a plug-in module in (or retro-fitted to) an existing digital tomosynthesis X-ray modality (such as shown in FIG. 2). The invention is intended to enhance the accuracy in determining the acquisition geometry of the tomosynthesis X-ray modality at the exact moments of the acquisition events. By providing a technical implementation that can be retro-fitted to an existing system, the advantages of the invention can thus be applied to any existing tomosynthesis X-ray modality. The accuracy of the acquisition geometry is vital in performing the image reconstruction on the acquired images.

In order to achieve enhanced accuracy in determining the acquisition geometry, a number of digital clocks [300] are associated with each movable image modality component [200] that determines the acquisition geometry. In principle, the components under consideration are limited to those contributing to the movement of the X-ray source or the detector position and orientation during the tomographic acquisition trajectory.

The principle of the invention is based on collecting a number of positional data records for all the mentioned movable components during their transgression on the tomographic acquisition trajectory. The positional data records do not need to be taken at the same moments in time (as was often a requirement for systems described in the art), but may be recorded at different moments for the different movable image modality components. These (randomly) chosen positional events (i.e. moments at which the positional data are recorded) are then marked (or associated) with a timestamp that is based on the time signal provided by the digital clock associated with the particular movable image modality component in question. What happens is that during the entire tomographic movement a number of (preferably, a high number—at least 2 and preferably 50-100) positional events are recorded and time-stamped with the digital clocks' time signal.

An essential aspect of the invention is that the clocks have a sufficiently similar accuracy. They are preferably of the same type. In addition, the clocks are synchronized at a predetermined moment in time that is not too much in advance of the tomographic acquisition itself. This is preferable to prevent that clocks would drift too far apart from each other in the period of time between the synchronisation and the collection of the positional data. Not only are the digital clocks that are associated with the movable components synchronized, but also the digital clock that is associated with the digital X-ray detector.

As explained before, the synchronization takes place ahead of the tomographic acquisition. The synchronization signal is preferably transmitted to all digital clocks by means of a hard-wired physical electrical connection [301], but other embodiments of signal carriers may be envisaged such as for instance an optical connection, galvanically separated connection, a wireless connection (such as for instance a radio-, Bluetooth- or wifi-connection). A physical electrical connection carries away the preference as it ensures the most reliable and fastest trigger signal possible to perform such a synchronization. Moreover a single hard-wired connection is practically very easy to implement.

The synchronization signal resets all digital clocks to an identical time signal ("zero" time), and may be triggered by any part of the image modality (such as the modality workstation, the positioner module itself, or a simple synchronizer contact button).

The result of this synchronisation of the clocks ahead of the tomographic acquisition is that all positional events (that take place at the movable components) can immediately receive an accurate time stamp matching the digital clocks' time. The movable components' associated clock runs synchronous with all other clocks. The time-stamping can take place without the risk of suffering from any latency, since the module that performs the time-stamping (i.e. performs the association of the time-stamp with the positional data of the event into a positional data record) is directly connected to the clock signal. The synchronisation of the digital clocks ensures that all recorded time-stamped data are accurately recorded relative to the "zero" time signal.

The positioner module has a number of distinct functional entities or components, such as; an input interface [311], an output interface [312], a memory [303] and a processing unit [304]. The input interface [311] is configured to receive time stamped positional information from the multiple movable image modality components [200], as well as query requests providing a certain time stamp for which the positional data for all movable image modality components are subsequently calculated and provided over the output interface [312].

The positioner module further comprises a processing unit [304] that may be envisaged as a programmable computer module or as a dedicated pre-programmed logical circuit (implemented as e.g. an FPGA, or alike) but performing the same functionality. The processing unit is configured as to perform the following functions:

1) it receives incoming positional event data from the different movable image modality components during their progression along the tomographic acquisition path, these positional events are time-stamped by the synchronized time signals provided by the respective associated digital clock of said component, and the positional event data (comprising the positional data and the time-stamp) are received by the input interface of the positioner module.
2) The time-stamped positional event data are subsequently stored into the memory of said positioner module upon receipt at the input interface. The time-stamped positional data are recorded in a list or a table which may be queried later to retrieve the stored information.
3) Subsequently, the input interface of the positioner module may receive queries for positional event data at a certain time event (for instance from the modality workstation). These queried time events should obviously fall within the period for which positional data are recorded in the memory of the positioner module. The query is received by the input interface and forwarded to the processing unit which will identify the query as a query request.
4) The processing unit will then calculate positional information data for all movable image modality components at the queried time. The calculation is based on interpolation of the positional data available in the records stored in the memory, and will return a calculated (interpolated) positional data response for the exact queried time event through the output interface of the positioner module.

So, when all collected and recorded positional data records have a synchronized timeline, it will be possible to align the different timelines for all movable components (and the timeline for the acquisition events at the digital detector). After the completion of the tomographic acquisition trajectory, multiple accurately time-stamped events will have been recorded. In the assumption that for a substantive part of the acquisition trajectory, the movement speed of the movable image modality components is constant (or at least known), it will be possible to derive additional intermediate positional data points from the recorded positional event data through interpolation.

Thanks to this, it will be possible to calculate (or estimate) very accurate positional information for any of the movable image modality components at any point in time during the tomographic acquisition cycle. As such, can the acquisition geometry of the tomographic system be accurately determined based on this accurately determined positional information for the involved modality components, and this for any point in time during the tomographic acquisition cycle.

So, in order to perform the image reconstruction, it remains that the modality workstation (which will perform the actual calculations of the image reconstruction) still needs to query the positioner module for the time-stamps associated with the acquired images in order to obtain their respective accurate acquisition geometries during acquisition. This query action can be performed either during or after completion of the tomographic acquisition cycle.

In an alternative embodiment, some essential components of the invention may be physically integrated into parts of the digital tomosynthesis X-ray modality. So can the digital clocks for instance be integrated into the respective movable image modality component to which such a clock is associated, or be integrated for instance into the digital X-ray detector. This approach would mean that a supplementary hardware module carrying the clock, the synchronisation contact, and some communication interfaces to at least export the time signal for association to the positional data, should be foreseen. This approach is actually preferred over the one where the digital clocks would reside in the positioner module, as it guarantees the best proximity between the component triggering the positional event and the clock itself; of which respectively the positional data and time-stamp need to be associated in a positional event message that is sent to the positioner module for recording and storing in memory. In the latter embodiment of the invention, the movable image modality component will in itself associate the data of a positional event with its time-stamp.

In a yet alternative embodiment, not only a synchronization signal is given prior to the start of the tomographic acquisition cycle, but also a "MoveEnable" signal is generated at either the modality workstation or by the positioner module itself. In the latter case, this "MoveEnable" signal would then be based on an earlier signal indicating the start of the tomographic acquisition cycle. The "MoveEnable" signal determines the start of the guaranteed linear movement of all movable contributing components of the tomographic modality. The "MoveEnable" signal is thus defined as a delayed signal based on an earlier signal indicating the start of the tomographic acquisition cycle that ensures that all movable image modality components are moving in a linear fashion. This delay is determined by the last (i.e. slowest to ramp up) movable component to achieve its linear velocity, after a ramp-up phase from stand-still. The "MoveEnable" signal will trigger the positioner module to start acquiring positional information from the different involved movable components. The advantage of this approach is that it is assured that any recorded positional events from the movable components show a linear relation between displacement and progressed time, and thus are allowing easy linear interpolations rather then having to compensate the non-linearities using ramp up and slow-down speed profiles for each of the movable components.

The "MoveEnable" signal can be calculated as an offset from the start-signal initiating the entire acquisition sequence (since it is determined by the last component that reaches its linear velocity).

In order to be able to implement the system of this invention into a tomosynthesis X-ray modality, it is a prerequisite for the modality that it firstly can perform a tomosynthesis acquisition sequence independently. This means that the digital X-ray modality should be capable of independently performing a sequence of modality component movements, and wherein at certain X-ray source and digital detector positions a predefined number of digital radiography acquisitions are performed. Such a modality thus may be programmed to perform such a coordinated sequence independently, i.e. without further user intervention. This is an essential requirement for the modality because the positioner or other component of the invention does not interfere with the performing of the tomographic movement itself.

A further prerequisite for such a modality is—secondly—that it can produce digital positional information output, meaning that the positional information of the movable image modality components is digitally outputted over an interface such that said digital positional information can be read out in a digital format and can be subsequently combined with said digital clock timestamps. The movable image modality components should be capable of generating positional events which then trigger the component that associates the digital clock signal with it, in order to collect and store the positional data with their respective time stamps in the memory of the positioner module.

In practice, the positional events of the different movable image modality components are triggered by the movable image modality component itself; meaning that the movable image modality component generates at certain time based and/or positional intervals a positional event. The positional data of such a positional event may then be combined with the digital clock timestamp by the modality component which reads the timestamp from the digital clock associated with it.

The invention claimed is:

1. A system for calculating positional information of multiple movable image modality components for an acquisition event that occurs during a tomographic image capture sequence, comprising:
    a positioner module, comprising
        an input interface configured to receive time-stamped positional information from said multiple moveable image modality components at multiple time intervals during said tomographic image capture sequence, and said input interface configured to receive a time-stamp value query of said acquisition event,
        a memory to store said time-stamped positional information for said multiple moveable image modality components at said multiple time intervals,
        processor that calculates positional information by interpolation of said stored time-stamped positional information of said movable image modality components for a time-stamp value query of said acquisition event, wherein the interpolated results are calculated relative to a synchronization signal, and
        an output interface to provide positional information on all of said moveable image modality components in response to said time-stamp value query calculated by said processing unit, and
    a clock associated with each of said multiple movable modality components to provide a time-stamp for each positional event of said movable modality components at multiple time intervals during said tomographic image capture sequence, wherein each of said clocks is interconnected in order to accept said synchronization signal to synchronize the times of said clocks.

2. The system of claim 1, further comprising a clock that is associated with an X-ray detector and that associates a time-stamp with an acquisition event performed by said X-ray detector, said clock being interconnected with said clocks associated with said movable modality components in order to accept said synchronization signal to synchronize the time of said clock associated with said X-ray detector.

3. The system of claim 1, wherein said positioner module and digital clocks are integrated into a physical enclosure for retrofitting into an existing tomosynthesis X-ray modality.

4. The system of claim 2, wherein said positioner module and digital clocks are integrated into a physical enclosure for retrofitting into an existing tomosynthesis X-ray modality.

5. A tomosynthesis X-ray modality system comprising the system of claim 1, and wherein said movable image modality components are embodied as:
    a set of at least two motor controllers that are physically controlling the movement of an X-ray source, and that enable said X-ray source to perform a tomosynthesis acquisition trajectory,
    at least one motor controller that is physically controlling the linear movement of an X-ray imaging detector, and that enable said digital image X-ray detector to perform a tomosynthesis acquisition trajectory, and
    a modality controller, controlling said motor controllers in order to synchronize their movements to perform a tomosynthesis acquisition trajectory after a start signal.

6. A tomosynthesis X-ray modality system comprising the system of claim 2, and wherein said movable image modality components are embodied as:
    a set of at least two motor controllers that are physically controlling the movement of an X-ray source, and that enable said X-ray source to perform a tomosynthesis acquisition trajectory,
    at least one motor controller that is physically controlling the linear movement of an X-ray imaging detector, and that enable said digital image X-ray detector to perform a tomosynthesis acquisition trajectory, and a modality controller, controlling said motor controllers in order to synchronize their movements to perform a tomosynthesis acquisition trajectory after a start signal.

7. A method for determining positional information of multiple movable modality components for use in determining the acquisition geometry of a tomographic system, comprising the steps of:

synchronizing a set of digital clocks that are individually associated with said multiple movable modality components, by giving an electric synchronization signal over an electrical connection interconnecting each of said clocks, receiving and storing in a memory multiple time-stamped positional event data from said multiple movable modality components during a tomographic acquisition sequence, said positional event data generated from positional events that are being triggered by said multiple movable modality components, and at which moment a time-stamp is associated with said positional event based on the time signal of the respective associated clock at said positional event, receiving a query for a time event, and calculating the positional data for all movable image modality components for said time event by interpolation of the positional data stored in said memory, and outputting the positional data for all movable image modality components to an output interface.

* * * * *